(12) United States Patent
Clevenger et al.

(10) Patent No.: US 10,596,304 B2
(45) Date of Patent: Mar. 24, 2020

(54) ANTI-INFECTIVE FUNCTIONALIZED SURFACES AND METHODS OF MAKING SAME

(71) Applicant: Orthobond Corp., North Brunswick, NJ (US)

(72) Inventors: Randell Clevenger, North Plainfield, NJ (US); Thomas J. Dennes, Parkesburg, PA (US); Jeffrey Schwartz, Princeton, NJ (US)

(73) Assignees: Orthobond Corporation, North Brunswick, NJ (US); The Trustees of Princeton University, Princeton, NJ (US)

( * ) Notice: Subject to any disclaimer, the term of this patent is extended or adjusted under 35 U.S.C. 154(b) by 177 days.

(21) Appl. No.: 15/497,909

(22) Filed: Apr. 26, 2017

(65) Prior Publication Data

US 2017/0224882 A1  Aug. 10, 2017
US 2018/0099075 A9  Apr. 12, 2018

Related U.S. Application Data

(63) Continuation of application No. 12/712,031, filed on Feb. 24, 2010, now abandoned.

(60) Provisional application No. 61/155,324, filed on Feb. 25, 2009.

(51) Int. Cl.

| | | |
|---|---|---|
| A01N 25/10 | (2006.01) | |
| A61L 31/16 | (2006.01) | |
| A01N 25/08 | (2006.01) | |
| A61L 31/02 | (2006.01) | |
| C07F 9/38 | (2006.01) | |

(52) U.S. Cl.
CPC .............. *A61L 31/16* (2013.01); *A01N 25/08* (2013.01); *A01N 25/10* (2013.01); *A61L 31/022* (2013.01); *C07F 9/3821* (2013.01); *A61L 2300/208* (2013.01); *A61L 2300/404* (2013.01)

(58) Field of Classification Search
CPC ........ A01N 25/10; A01N 25/08; A01N 59/16; A01N 59/20; A01N 31/12; A61L 31/16; A61L 31/022; A61L 2300/208; A61L 2300/404; C07F 9/3821
See application file for complete search history.

(56) References Cited

U.S. PATENT DOCUMENTS

| | | |
|---|---|---|
| 4,879,135 A | 11/1989 | Greco et al. |
| 5,078,782 A | 1/1992 | Nielsen et al. |
| 7,459,167 B1 | 12/2008 | Sengupta et al. |
| 2005/0027360 A1 | 2/2005 | Webb |
| 2005/0147750 A1 | 7/2005 | Jacobs et al. |
| 2006/0194008 A1* | 8/2006 | Schwartz ................ A61L 27/32 428/34.4 |
| 2007/0077348 A1 | 4/2007 | Lu et al. |
| 2007/0196663 A1 | 8/2007 | Schwartz et al. |
| 2007/0292355 A1 | 12/2007 | Tamarkin et al. |
| 2009/0232867 A1 | 9/2009 | Domb et al. |
| 2016/0115268 A1 | 4/2016 | Clevenger et al. |

FOREIGN PATENT DOCUMENTS

| | | |
|---|---|---|
| WO | 200100034 | 1/2001 |
| WO | 2009052352 | 4/2009 |

OTHER PUBLICATIONS

Park et al., "Antibacterial Activities of Polystyrene-Block-Poly (4-Vinyl Pyridine) and Poly (Styrene-Random-4-Vinyl Pyridine)" European Polymer Journal 40 (2004) 2318-2822, 5 pages.

Dennes et al., A Nanoscale Adhesion Layer to Promote Cell Attachment on PEEK, Feb. 18, 2009, J. Am. Chem. Soc., vol. 131, pp.

Shard et al., "Surface Oxidation of Polyethylene, Polysthylene, Polystyrene, and PEEK: The Synthon Approach", 1992, Macrmolecules, vol. 25, pp. 2053-2054.

* cited by examiner

*Primary Examiner* — Ali Soroush
(74) *Attorney, Agent, or Firm* — Venable LLP (57) ABSTRACT

Devices are provided which are functionalized to include surface regions having anti-infective agents. Methods are provided for functionalizing various material surfaces to include active surface regions for binding anti-infective agents. Methods are provided by which anti-infective moieties or agents are bonded to functionalized surfaces.

9 Claims, 3 Drawing Sheets

ANTI-INFECTIVE FUNCTIONALIZED SURFACES AND METHODS OF MAKING SAME

CROSS-REFERENCE TO RELATED APPLICATIONS

This application claims the benefit of U.S. Provisional Patent Application Ser. No. 61/155,324, filed Feb. 25, 2009, the entirety of which is incorporated herein by reference.

FIELD OF THE INVENTION

The present invention relates to substrates with anti-infective surfaces. In particular, methods are provided for functionalizing various material surfaces to include active surface regions for binding anti-infective agents.

BACKGROUND OF THE INVENTION

An activated, or functionalized, layer that is bonded or otherwise disposed on the surface of a substrate is useful as an interface between the substrate and other materials such as organic or metallic materials. This functionalized layer allows the substrate to react with and to bind to the organic or metallic material.

The need for control of infection is a vital concern for many, from public health officials, hospital and school administrators and the like, to private citizens. Typically, control of infection can be achieved by the topical application of disinfectants, antiseptics, antibacterials and the like to surfaces likely to be contacted by infectious agents. Common disinfectants include active chlorine such as hypochlorites, chloramines, dichloroisocyanurate and trichloroisocyanurate, wet chlorine, chlorine dioxide and the like, active oxygen, including peroxides, such as peracetic acid, potassium persulfate, sodium perborate, sodium percarbonate and urea perhydrate, iodine compounds such as iodpovidone, iodine tincture, iodinated nonionic surfactants, concentrated alcohols such as ethanol, n-propanol and iso-propanol and mixtures thereof; 2-phenoxyethanol and 1- and 2-phenoxypropanols, phenolic compounds, cresols, halogenated phenols, such as hexachlorophene, triclosan, trichlorophenol, tribromophenol, pentachlorophenol, Dibromol and salts thereof, cationic surfactants, including quaternary ammonium cations such as benzalkonium chloride, cetyl trimethylammonium bromide or chloride, didecyldimethylammonium chloride, cetylpyridinium chloride, benzethonium chloride and others, and non-quaternary compounds, such as chlorhexidine, glucoprotamine, octenidine dihydrochloride etc.); strong oxidizers, such as ozone and permanganate solutions; heavy metals and their salts, such as colloidal silver, silver nitrate, mercury chloride, phenylmercury salts, copper, copper sulfate, copper oxide-chloride and the like, and strong acids (phosphoric, nitric, sulfuric, amidosulfuric, toluenesulfonic acids) and alkalis (sodium, potassium, calcium hydroxides). However, many of these compounds are harmful to mammalian tissue. Moreover, these compounds only have a short-term effect, and need to be reapplied constantly.

Antibiotics can be administered to stop infection in individuals. However, such administration is not always effective. Numerous medical applications, including orthopaedic, trauma, spine and general surgery applications, where the potential for infection is a serious concern, are not amenable to simple application of antiseptic or treatment with antibiotics. For example, infection can be a devastating complication of a total joint arthroplasty (TJA). While some infections may be treated by antibiotic suppression alone, more aggressive therapies, such as two-stage re-implantation, are often required. The treatment of post-arthroplasty infections in 1999 cost over $200 million in the US alone. Spangehl, M. J., et al., *J. Bone Joint Surg. Am.*, 1999, 81(5), 672-682. TJA infections occur when bacteria colonize the surface of the implant. These species then form a resistant biofilm on the implant surface, which nullifies the body's normal antibody response.

External fixation devices provide temporary but necessary rigid constraints to facilitate bone healing. However, patients risk pin-tract infection at the site extending from the skin-pin interface to within the bone tissue. Such complications can result in sepsis and osteomyelitis, which could require sequestrectomy for correction. Even the most stringent pin-handling and post-procedure protocols have only a limited effect. Studies have shown that such protocols do not reduce the chance of infection. Davies, R., et al. *J. Bone Joint Surg. Br.*, 2005, 87-B, 716-719.

In minimally-invasive spine fusions, pedicle screws are first implanted in the bone of the vertebrae, and then rods are fixed into the heads of the screws to immobilize and stabilize the affected segments. Screws and rods pass through the patient's skin into the spine space via a cannulated channel. As in external fixation, screws and rods are also prone to pin-tract infections; due to the implants' pathway through the skin, the chance of contacting and/or passing harmful bacteria is greatly increased.

Catheters and shunts are placed in any number of body cavities and vessels to facilitate the injection, drainage, or exchange of fluids. Infections are common in catheter placements and are largely dependent on how long the patient is catheterized. For example, Kass reports an infection rate of virtually 100% for patients with indwelling urethral catheters draining into an open system for longer than 4 days. Kass, E. H., *Trans. Assoc. Am. Physicians*, 1956, 69, 56-63.

Therefore, there is a need for anti-infective surfaces that may be employed in locations particularly susceptible to hosting infectious agents, such as public places, common areas of buildings, fixtures and the like. Moreover, there is a need for substrates and materials with anti-infective surfaces, such as medical devices including implants, screws, rods, pins, catheters, stents, surgical tools and the like which could prevent infections by proactively killing bacteria that attempt to colonize the device surface both pre- and post-operatively.

SUMMARY OF THE INVENTION

In accordance with one or more embodiments methods are provided for functionalizing various material surfaces to include an active surface region to which are bound anti-infective agents.

Depending on the application, a surface of interest is functionalized in accordance with a suitable functionalization method and an anti-infective agent is disposed on the functionalized surface.

Virtually any surface which may be functionalized is suitable for the inclusion of an anti-infective agent in accordance with the disclosed embodiments. Examples of such surfaces include metals, alloys, polymers, plastics, ceramics and glass. Therefore, the anti-infective surfaces as described herein may be applied universally through any environment, for example, in the environment of a surgical procedure or throughout an operating room or hospital, thereby eliminating many, if not all, sources of infection simultaneously and continuously.

Functionalization of substrates in accordance with the present invention may be achieved in a variety of ways. For example, it is possible to functionalize the surface of a polymer substrate such as but not limited to polyamides, polyurethanes, polyesters, polyketones, polyethers, polyimides, aramides, polyfluoroolefins, epoxies, silicones or composites containing these polymers with an oxide, alkoxide or mixed oxide-alkoxide layer using an alkoxide precursor. Such functionalized polymer surfaces can be used to covalently bond subsequent material or layers thereof on the surface, which in the present invention includes anti-infective moieties. For example, substrates that contain acidic protons, such as —OH or —NH groups, are functionalized by their reaction with Group IV alkoxides. This procedure yields a molecular adhesion species that is bound to the surface of the bulk polymer, but is limited to materials that have acidic groups on their surface.

It is further possible to form an adherent coating layer that may be further functionalized with adherent species by heating a self-assembled layer of a functionalized phosphonic acid on the native oxide surface of a substrate or a deposited oxide derived from an alkoxide precursor. A plurality of one or more anti-infective coating moieties may be bonded to the functional group of at least one functionalized organophosphonate moiety. Such native oxides are found on metals including but not limited to titanium and its alloys; stainless steel; cobalt chrome alloys; and nickel, molybdenum, tantalum, zirconium, magnesium, and alloys containing them It is yet further possible to bond anti-infective species to the functional group of a phosphonic acid before attaching said acid to a native oxide or an oxide derived from an alkoxide precursor. Such native oxides are found on metals including but not limited to titanium and its alloys; stainless steel; cobalt chrome alloys; and nickel, molybdenum, tantalum, zirconium, magnesium, and alloys containing them In another embodiment, functionalization of a silicon surface may be achieved by a process wherein a self-assembled film of an organophosphonic acid is bonded to a native or synthesized oxide-coated Si surface as a film of the corresponding phosphonate. The phosphonate film is functionalized to enable covalently coupling biological molecules, ranging in size from small peptides to large multi-subunit proteins, to the Si surface.

In still a further embodiment, anti-infective peptide-modified surface-bound phosphonate films may be bonded to metal surfaces and polymer surfaces functionalized with alkoxide-derived oxides.

It is expected the anti-infective surface modification methods described herein may eliminate the need for passivation, frequently a necessary step in the processing of metal implants. Processes as disclosed herein provide layers bonded to metal surfaces and transform the surface oxides into chemically- and physically-robust species, thus eliminating the source of corrosion in devices such as metal implants.

Anti-infective agents as discussed herein may include bactericidal and bacteriostatic agents including disinfectants, antiseptics and antibiotics. Not all bactericidal and bacteriostatic agents may be used as antiseptics on mammalian tissue as they may have adverse effects thereon. Some embodiments of the present invention may apply to uses that do not involve contact of an anti-infective surface with mammalian tissue, such as interior surfaces of plumbing fixtures, building materials, ductwork, clean rooms, etc. In such applications certain anti-infective agents may be used, such as disinfectants, which would not be appropriate for use in applications in which contact with mammalian tissue was contemplated or possible.

In some embodiments compounds that may be used as antiseptics for use in humans include properly diluted chlorine preparations such as Daquin's solution, 0.5% sodium or potassium hypochlorite solution, pH-adjusted to pH 7-8, or 0.5-1% solution of sodium benzenesulfochloramide, some iodine preparations, such as iodopovidone, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid, some phenolic compounds, such as hexachlorophene, triclosan and Dibromol, and cation-active compounds, such as 0.05-0.5% benzalkonium, 0.5-4% chlorhexidine, 0.1-2% octenidine solutions.

In further embodiments anti-infective agents used in applications which involve possible contact with mammalian tissue may include quaternary ammonium compounds such as choline and choline derivatives, quaternary ammonium dendrimers, silver, copper, and cationic species; silver and copper.

As will be apparent to those skilled in the art, the functionalization method employed to bond or otherwise attach a particular anti-infective agent in accordance with the present invention is dependent on the chemical nature of the anti-infective agent.

Devices made in accordance with the present disclosure provide a multitude of clinical benefits. For example, in partially external devices, anti-infective surfaces thereof may kill bacterial species at the device-skin interface, thus preventing pin-site infections. Devices including an anti-infective surface may prevent the colonization by infectious species of implanted surfaces, potentially reducing the incidence of deep infection, especially in high-risk populations. In catheters and shunts with anti-infective surfaces the potential for infection is minimized by killing bacteria traveling up the intubated pathway into the patient. Another example is in total hip arthroplasties; anti-infective hip stems may kill bacterial species and inhibit biofilm formation at the device-tissue interface, preventing the bacterial colonization of the hip replacement, which can lead to loosening due to infection and could require cost and painful hip revision surgery. The anti-infective agent is highly stable under physiological conditions. The anti-infective agent does not leach from its material host, so there is no undesirable secondary result. Due to its nanometer scale, the anti-infective agent does not interfere with desired mechanical surface features that may be critical to the function of device such as an implant. The anti-infective agent is not visible to the naked eye and does not obscure identifying features including colored anodization or product markings.

Devices in accordance with the present disclosure are not limited to medical devices. For example, devices embodying the present disclosures may include fixtures, structures, fittings, barriers, and the like having anti-infective surfaces.

DETAILED DESCRIPTION OF THE PREFERRED EMBODIMENTS

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

In general, in accordance with one or more embodiments methods are provided for functionalizing various material surfaces to include an active surface region to which are bound anti-infective agents. Depending on the application, a surface of interest is functionalized and an anti-infective agent is disposed on the functionalized surface to provide devices having anti-infective surfaces.

Figure 1:
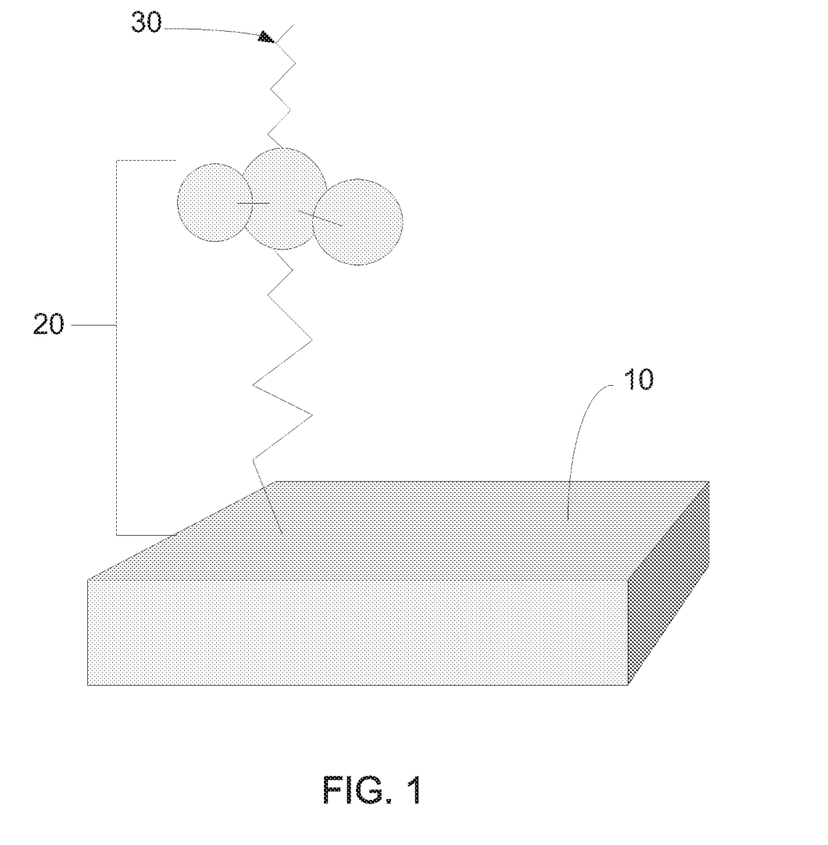
FIG. 1 depicts a schematic of an anti-infective agent bound to a surface in accordance with at least one embodiment of the present disclosure.

Now referring to FIG. 1, in general a surface 10 in accordance with the present disclosure includes a functionalizing layer 20 and an anti-infective agent 30.

Surface 10 may be virtually any material which is amenable to receiving a functionalizing layer 20. Examples of such materials include metals, alloys, polymers, plastics, ceramics, silicon, glass and surfaces with acidic protons, such as —OH or —NH groups.

Functionalizing layer 20 may be any layer suitable for a particular application. The nature and composition of functionalizing layer 20 is dependent on the surface 10 that is intended to include an anti-infective agent 30 and the anti-infective agent 30 that is to be bound to the functionalizing layer 20. For example, as described in greater detail hereinbelow, it is possible to functionalize a polymer substrate surface 10 with an oxide, alkoxide or mixed oxide-alkoxide layer using an alkoxide precursor. Such functionalized polymer surfaces can be used to covalently bond subsequent material or layers of anti-infective agent 30 on the surface.

Other functionalizing layers 20 may include functionalized phosphonic acids disposed on a native oxide of a substrate surface; functionalized phosphonic acids disposed onto an oxide layer, either directly deposited onto an underlying substrate or derived from an alkoxide precursor; for surfaces that contain acidic protons, such as —OH or —NH groups, reacting same with Group IV alkoxides; for surfaces with a silicon surface, a self-assembled film of a phosphonic acid bound to the native or synthesized oxide-coated Si surface as a film of the corresponding phosphonate; and the like.

Metal surfaces which may be employed include titanium and its alloys; stainless steels; cobalt chrome alloys; nickel, molybdenum, tantalum, zirconium, magnesium, manganese, niobium, and alloys containing them; and the like.

Anti-infective agents 30 that may be employed in connection with embodiments herein may include bactericidal and bacteriostatic agents including disinfectants, antiseptics and antibiotics. Disinfectants include active chlorine such as hypochlorites, chloramines, dichloroisocyanurate and trichloroisocyanurate, wet chlorine, chlorine dioxide and the like, active oxygen, including peroxides, such as peracetic acid, potassium persulfate, sodium perborate, sodium percarbonate and urea perhydrate, iodine compounds such as iodopovidone, iodine tincture, iodinated nonionic surfactants, concentrated alcohols such as ethanol, n-propanol and isopropanol and mixtures thereof; 2-phenoxyethanol and 1- and 2-phenoxypropanols, phenolic compounds, cresols, halogenated phenols, such as hexachlorophene, triclosan, trichlorophenol, tribromophenol, pentachlorophenol, Dibromol and salts thereof, cationic surfactants, including quaternary ammonium cations such as benzalkonium chloride, cetyl trimethylammonium bromide or chloride, didecyldimethylammonium chloride, cetylpyridinium chloride, benzethonium chloride and others, and non-quaternary compounds, such as chlorhexidine, glucoprotamine, octenidine dihydrochloride etc.); strong oxidizers, such as ozone and permanganate solutions; heavy metals and their salts, such as colloidal silver, silver nitrate, mercury chloride, phenylmercury salts, copper, copper sulfate, copper oxide-chloride and the like, and strong acids (phosphoric, nitric, sulfuric, amidosulfuric, toluenesulfonic acids) and alkalis (sodium, potassium, calcium hydroxides).

Not all bactericidal and bacteriostatic agents may be used as antiseptics on mammalian tissue as they may have adverse effects thereon. It will be apparent to those skilled in the art that some embodiments of the present invention may apply to uses that do not involve contact of an anti-infective surface with mammalian tissue, such as the fabric used for surgical barriers and the interior surfaces of plumbing fixtures, building materials, ductwork, clean rooms, etc. In such applications certain anti-infective agents may be used, such as disinfectants, which would not be appropriate for use in applications in which contact with mammalian tissue would be contemplated or possible.

The following are some compounds that may be used as antiseptics for use in humans: properly diluted chlorine preparations such as Daquin's solution, 0.5% sodium or potassium hypochlorite solution, pH-adjusted to pH 7-8, or 0.5-1% solution of sodium benzenesulfochloramide, some iodine preparations, such as iodopovidone, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid, some phenolic compounds, such as hexachlorophene, triclosan and Dibromol, and cation-active compounds, such as 0.05-0.5% benzalkonium, 0.5-4% chlorhexidine, 0.1-2% octenidine solutions.

In preferred embodiments anti-infective agents used in applications which involve possible contact with mammalian tissue include but are not limited to quaternary ammonium compounds such as choline and choline derivatives, quaternary ammonium dendrimers, silver, copper, and cationic species. Quaternary ammonium compounds ("quats") with long alkyl chains show proven biocidal properties by disruption of cell walls. Nakagawa, Y., et al., *Appl. Environ. Microbiol.*, 1984, 47:3, 513-518, incorporated by reference herein in its entirety. The quaternary ammonium cation functional group draws in and disrupts the cell membrane of the bacteria. Quaternary ammonium dendrimers show similar biocidal activity naturally and when combined with functional groups or molecules with biocidal properties, can further enhance antimicrobial activity by increased loading. Silver and copper have observed oligodynamic effects on microbes. Research suggests that silver and copper ions denature proteins in the target organism by binding to reactive groups. This binding results in precipitation and deactivation. Silver has also been shown to interfere with enzymes and metabolic processes. Cationic species are electrostatically attracted to bacterial cell walls, which are negatively charged. Cationic antimicrobial peptides have been shown to have inhibitory effects on the regulatory mechanisms of the target organism.

In certain applications, it may be useful to functionalize the anti-infective agent, in which case the the anti-infective agent may include an acid functionalized group, wherein the acid is for example an organophosphonic, carboxylic, sulfonic, sulfinic, phosphinic, phosphonic, phosphoric or hydroxamic acid.

Figure 2:
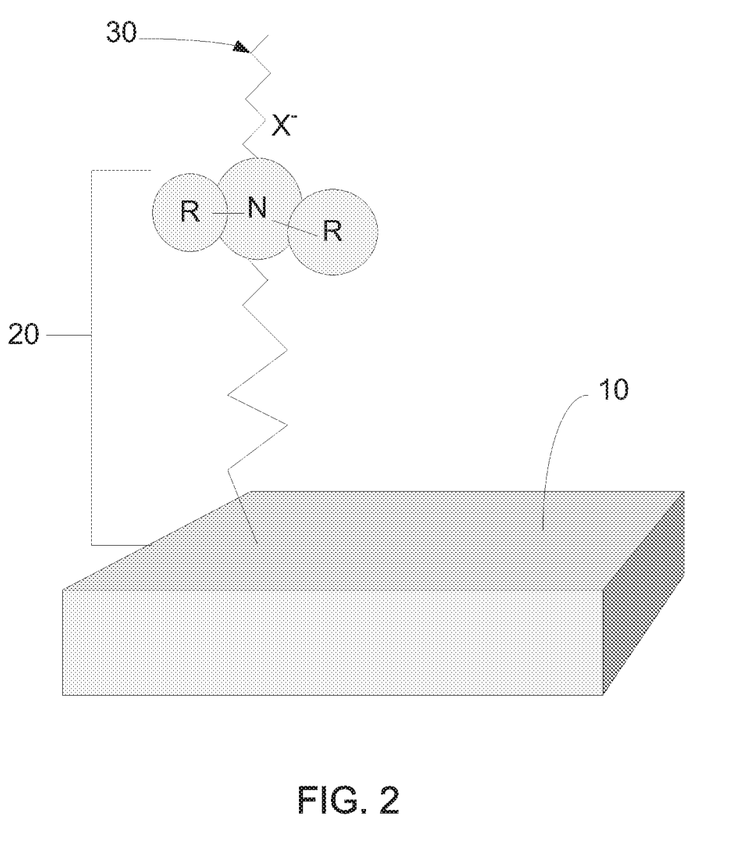
FIG. 2 depicts an anti-infective agent bound to a surface in accordance with at least one embodiment of the present disclosure.

Now referring to FIG. 2 an embodiment of an anti-infective surface employs a Self-Assembled Monolayer Phosphonate (AI-SAMP) surface modification 20 covalently bound to the surface 10 of an implantable material. Here, the anti-infective agent 30 is a quaternary ammonium cationic functional group which is bound to the surface via the SAMP. Covalent bonding creates an exceptionally strong attachment between the surface treatment and the material to which it is applied. Schwartz, J., et al., *Mat. Sci. Engr. C,* 2003, 23, 395-400, the entirety of which is incorporated herein by reference. Because SAMP is one molecule thick, it completely covers the material to which it is applied and assures total implant coverage regardless of the type or texture of the implant material. Covalent binding of quaternary ammonium salts renders the quats insoluble, providing lasting anti-infective activity. See, e.g., Nakagawa, Y., et al., *Appl. Environ. Microbiol.,* 1984, 47:3, 513-518.

Figure 3:
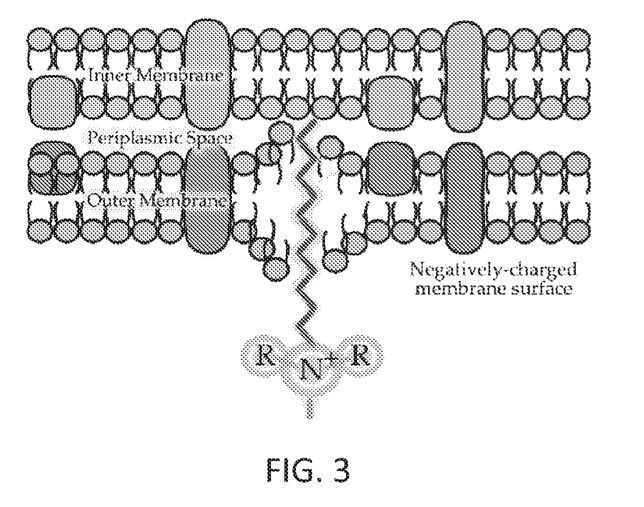
FIG. 3 depicts a mode of action of an anti-infective agent in accordance with at least one embodiment of the present disclosure

As shown in FIG. 3, the quaternary ammonium cation functional group draws in and disrupts the cell membrane of the bacteria.

Functionalization Methods

Several methods are suitable for functionalizing a surface. As will be apparent to those skilled in the art, the functionalization method employed to bond or otherwise attach a particular anti-infective agent in accordance with the present invention is dependent on the chemical nature of the anti-infective agent and the surface of interest.

It is possible to functionalize a polymer substrate surface such as but not limited to surfaces of polyamides, polyurethanes, polyesters, polyketones, polyethers, polyimides, aramides, polyfluoroolefins, polyetheretherketones, polyetherketoneketones, epoxies, silicones or composites containing these polymers with an oxide, alkoxide or mixed oxide-alkoxide layer using an alkoxide precursor. Such functionalized polymer surfaces can be used to covalently bond subsequent material or layers of anti-infective agent on the surface. The polymer surface may be coated with a layer of metal oxide (oxide adhesion layer).

In one embodiment the polymer surface may be coated with a continuous oxide adhesion layer, i.e., a layer that is formed by a matrix of individual molecules that are chemically bonded and linked to each other, as opposed to individual molecules covering the surface. In this embodiment metal alkoxide molecules are bonded together on at least a portion of a polymer surface to form a continuous layer and then converted to an oxide functionalizing layer.

It is further possible to form an adherent coating layer that may be further functionalized with adherent species by heating a self-assembled layer of a functionalized phosphonic acid on the native oxide surface of a substrate. This process, described in detail in U.S. Patent Application Publication 2004/0023048, the entirety of which is incorporated herein by reference, provides on the native oxide surface of a material a multi-segmented, phosphorous-based coating layer having a difunctional organophosphonic acid-based segment bonded to the native oxide surface of the material and a linking segment bonded to the organophosphonic acid-based segment. In accordance with this process, a phosphorous-based coating layer may be provided having a plurality of functionalized organophosphonate moieties bonded to the native oxide surface of a substrate by a phosphonate bond and a plurality of one or more anti-infective coating moieties, each coating moiety being bonded to the functional group of at least one functionalized organophosphonate moiety. When bonded by means of a metal complex, the metal complex is further characterized by being derived from a metal reagent, preferably a metal alkoxide reagent.

Other functionalization processes may be employed depending on the substrate to be functionalized and the anti-infective moiety desired. For example, it is possible to functionalize substrates that contain acidic protons, such as —OH or —NH groups, by their reaction with Group IV alkoxides. This procedure yields a molecular adhesion species that is bound to the surface of the bulk polymer, but is limited to materials that have acidic groups on their surface. This method is described in detail in Dennes, T. J. et al., High-Yield Activation of Scaffold Polymer Surfaces to Attach Cell Adhesion Molecules. *J. Am. Chem. Soc.* 2007, 129, 93-97; and Dennes, T. J.; Schwartz, J. Controlling Cell Adhesion on Polyurethanes. *Soft Matter* 2008, 4, 86-89, both of which are incorporated herein by reference in their entireties.

Organic SAM's may be covalently bonded to the surface of metal oxide or silicon oxide substrates. Forming a self-assembled organic monolayer on the surface of a metal oxide or silicon oxide substrate, may entail providing a metal oxide or silicon oxide substrate overlayer having a surface layer of alkoxides of transition metals selected from Group IVB, Group VB or Group VIB of the Periodic Chart covalently bonded thereto, wherein the alkoxides are bonded at the transition metal atoms to the surface oxygens of the substrate overlayer; and reacting the transition metal alkoxide surface layer with an organic compound capable of reacting with the transition metal alkoxide to form an organic ligand covalently bonded to the transition metal, thereby forming an organic self-assembled monolayer on the surface of the substrate, covalently bonded at the transition metal atoms to the surface oxygens of the substrate. This method is described in detail in U.S. Pat. No. 6,146,767 (see e.g., col. 3, lines 1-22 and Examples), incorporated by reference in its entirety. Suitable acid functional groups that can react with metal alkoxides include for example carboxylic, sulfonic, sulfinic, phosphinic, phosphonic, phosphoric and hydroxamic acid.

For example, methods described in detail in U.S. Pat. No. 6,645,644 (see e.g., col. 4, lines 15-33 and Examples), incorporated by reference in its entirety, include forming a phosphate or phosphonate ligand layer covalently bonded to the surface of a hydroxide-bearing substrate, which includes coating a hydroxide-bearing substrate with phosphoric acid or an organic phosphonic acid and heating the coated substrate until the phosphoric acid or organic phosphonic acid covalently bonds to the substrate. When the substrate is a metal or metal alloy, the phosphoric acid forms an inorganic phosphate coating that is rich in free hydroxyl groups. Like transition metal monophosphate and polyphosphate coatings, the hydroxyl groups are available for the addition of an anti-infective agent.

In another embodiment, functionalization of a silicon surface may be achieved by a process wherein a self-assembled film of an organophosphonic acid is bonded to a native or synthesized oxide-coated Si surface as a film of the corresponding phosphonate. The phosphonate film is functionalized to enable covalently coupling biological molecules, ranging in size from small peptides to large multi-subunit proteins, to the Si surface. The linking of antibodies to such surfaces enables the selective recognition of a wide range of molecules, including antigens on the surfaces of bacterial pathogens and parasites. This method is described in detail in Midwood et al., Easy and Efficient Bonding of Biomolecules to an Oxide Surface of Silicon. *Langmuir* 2004, 20, 5501-5505, incorporated herein by reference in its entirety. Experimental details appear at page 5501, col. 2-page 5502, col. 2; see also discussion at pages 5502-5504 and accompanying figures.

In still a further embodiment, surface-bound phosphonate films may be used to functionalize titanium and alloys thereof (such as Ti-6Al-4V) to attach anti-infective peptides. As is known in the art titanium and its alloys have high mechanical strength and are resistant to chemical attack, and thus are favored materials for surgical implants which may contact bone. This method is described in detail in Gawalt et al., Bonding Organics to Ti Alloys: Facilitating Human Osteoblast Attachment and Spreading on Surgical Implant Materials" *Langmuir* 2003, 19, 200-204, incorporated herein by reference in its entirety. Experimental details appear at page 200 col. 2-page 201, col. 2; see also discussion at pages 201-204 and accompanying figures.

Metal Oxide Adhesion

Metal oxide adhesion techniques involve an oxide adhesion layer bonded to a surface thereof via coordination groups, wherein the oxide adhesion layer is a metal alkoxide, generally M—O—R wherein M is a metal atom. The oxide adhesion layer is one that has been subjected to a process such as but not limited to pyrolysis, microwaving, complete hydrolysis and/or partial hydrolysis. The technique is well suited for example to polymers or metals. Functionalized surfaces such as functionalized metals or polymers can be used to covalently bond subsequent material or layers of anti-infective agent on the surface.

Suitable polymeric substrates include any polymer that can be functionalized, and may include any of various substances comprising synthetic and/or natural polymer molecules. Examples of suitable polymer substrates include, but are not limited to, polyamides, polyurethanes, polyureas, polyesters, polyketones, polyimides, polysulfides, polysulfoxides, polysulfones, polythiophenes, polypyridines, polypyrroles, polyethers, silicones, polysiloxanes, polysaccharides, fluoropolymers, amides, imides, polypeptides, polyethylene, polystyrene, polypropylene, glass reinforced epoxies, liquid crystal polymers, thermoplastics, bismaleimide-triazine (BT) resins, benzocyclobutene polymers, Ajinomoto Buildup Films (ABF), low coefficient of thermal expansion (CTE) films of glass and epoxies, and composites including these polymers. The oxide adhesion layer adheres to the surface of the polymer by the covalent bonding between the coordinating group on the surface of the polymer and the metal of the metal alkoxide.

Alkoxides of transition metals are particularly useful for the present invention. Periodic Table Group 3-6 and 13-14 metals are desirable metals for compositions of the present invention. The preferred metals are Zr, Al, Ti, Hf, Ta, Nb, V and Sn, with the most preferred metals being Zr, Ti and Ta. Depending upon the position of the transition metal on the Periodic Table, the transition metal alkoxide will have from three to six alkoxide groups or a mixture of oxo and alkoxide groups. Preferred alkoxide groups have from 2 to 4 carbon atoms, such as ethoxide, propoxide, iso-propoxide, butoxide, iso-butoxide, tert-butoxide and fluoronated alkoxide. The most preferred metal alkoxides are zirconium tetra(tert-butoxide), titanium tetra(tert-butoxide), and tantalum pentaethoxide.

Methods of making compositions and devices in accordance with this embodiment include activating a polymer surface comprising the steps of a) contacting a metal alkoxide with the surface; and b) subjecting the metal alkoxide to conditions adequate to form an adhesion layer on the surface on the surface comprised of an oxide, alkoxide, or mixed oxide/alkoxide. The contacting step may be achieved by any suitable technique known to those skilled in the art such as but not limited to vapor or immersion deposition. The step of forming an oxide adhesion layer may be achieved by subjecting the metal alkoxide to conditions of pyrolysis, microwaving, complete hydrolysis or partial hydrolysis. When heating conditions are employed, it is preferred that the metal alkoxide is heated to between about 50° C. and the upper working temperature of the polymer.

In one embodiment metal alkoxide molecules may be bonded together on at least a portion of a polymer surface to form a continuous layer and then converted to an oxide functionalizing layer. One major advantage of a continuous layer is that the entirety of the surface that is covered by the continuous metal oxide adhesion layer is activated. A more comprehensive discussion of this process is described in detail in U.S. Patent Application Publication 2009/0104474, published Apr. 23, 2009, the entirety of which is incorporated herein by reference. This process provides functionalized polymer surfaces that can be used to covalently bond subsequent material or layers thereof on the surface. In general, the process involves depositing a metal alkoxide on a polymer, and heating the substrate, with or without hydrolysis (full or partial), so that the metal alkoxide molecules form a continuous metal oxide adhesion layer covalently attached to the polymer surface. For example, the molecules of metal alkoxide are first brought into reactive proximity to the polymer molecules such as by, but not limited to, vapor deposition, brush-on or immersion deposition methods known in the art. If an ultrathin layer is desired, vapor deposition is the preferred process. The deposited metal alkoxide molecules are then heated to between about 50° C. and the upper working temperature of the polymer (the heating should not be at or above the glass transition temperature of the polymer) to pyrolyze the metal alkoxides. During pyrolysis or hydrolysis, the individual metal alkoxide molecules are covalently bonded together forming a continuous metal oxide adhesion layer. The metal oxide adhesion layer may be thin, about 1 nm-1 μm, preferably about 2 nm, such that it is flexible. The thin layer allows the oxide adhesion layer to bend with the substrate material without cracking, peeling, or breaking. Using this functionalization method, in one embodiment, a polymer surface may include acidic functionality regions as well as regions coated with a metal alkoxide functionalized layer. In such embodiments the metal alkoxide functionalized layer may be viewed as filling in the spaces between the regions of acidic functionality. In accordance with another embodiment metal alkoxide functionalized layers may be applied to regions of polymer having acidic functionality.

Compositions in accordance with this embodiment include anti-infective agents bound via the oxide adhesion layer to the polymer substrate. Such additional anti-infective material may include but is not limited to quaternary ammonium compounds, quaternary ammonium dendrimers, silver, copper, and cationic species. A more complete, but not exhaustive, list of anti-infective agents are detailed hereinbelow. The usefulness of the additional anti-infective material will be apparent to those skilled in the art. For example, medical and orthopedic implant devices including anti-infective surface functionality minimizes infection. Likewise, anti-infective materials can be incorporated in clean room applications, water supply articles such as well pumps, water purification pipes and conduit and the like.

As described in further detail hereinbelow, copper and silver are exemplified as anti-infective materials.

The anti-infective material may be introduced to the oxide adhesion layer by techniques know to those of skill in the art, including but not limited to covalent bonding, evaporative, sputter or, immersion deposition. In some embodiments it may be desirable to subject the oxide adhesion layer to complete or partial hydrolysis prior to deposition of the additional material. In some embodiments it may be desirable to subject the deposited additional material to heat or microwave treatment.

In accordance with another embodiment the adhesion layer may be disposed on the substrate in a pattern or micropattern.

In accordance with another embodiment the anti-infective material may be disposed on the adhesion layer in a pattern or micropattern as described in further detail hereinbelow.

The oxide adhesion layer is reacted with an anti-infective material as discussed above to bind the anti-infective material to the polymer surface via the oxide adhesion layer. The additional material may be added by reaction with the oxide adhesion layer by various methods available in the art, such as but not limited to covalent bonding, evaporative, sputter, or immersion deposition. In one embodiment of the present invention, the material may be added using lithography, printing or stamping techniques to lay a pattern of material on to the oxide adhesion layer. The polymer surface may be completely coated with a photoresist, and exposed to UV light through a mask. The areas exposed to the UV light can be developed and removed, leaving openings in the photoresist and access to the polymer surface in small areas. These areas are functionalized with the metal oxide adhesion layer. The photoresist is then dissolved away leaving small patterned areas in the polymer surface that include the adhesion layer. The patterned areas are preferentially reactive toward anti-infective agents of choice.

In accordance with one embodiment, the oxide adhesion layer may be subjected to complete or partial hydrolysis prior to deposition of the anti-infective material to achieve the oxide adhesion layer with one or more alkoxide groups remaining on the metal atoms. Absorption of solutions of silver or copper salts, followed by reduction, enables the surface of the metal to be coated with particulate silver or copper, respectively. Formation of an adhesion layer of zirconium oxide also enables metallization of for example, a PEEK surface by absorption of a solution of either a silver salt (such as silver nitrate) or a copper salt (such as copper sulfate) followed by reduction with a reducing agent. For example, diethylaminoborane or sodium borohydride reduce the aforementioned salts to silver and copper metals, respectively, which are included in the oxide adhesion layer matrix.

In a prophetic embodiment, a zirconium oxide adhesion layer may also be grown on the native oxide surface of a metal such as titanium.

Examples of Anti-Infective Agents Using Metal Oxide Functionalization

It is believed that one of ordinary skill in the art can, using the preceding description and the following illustrative examples, make and utilize the compounds and articles of the present invention and practice the claimed methods. The following examples are given to illustrate the present invention. It should be understood that the invention is not to be limited to the specific conditions or details described in these examples.

EXAMPLES

Example 1. Metallization of Activated Polymers

Activated polymers of polyimides, aramides and Gore-Tex composites were produced as follows:

Formation of a zirconia thin film on polymer substrate:

All reagents were obtained from Aldrich and were used as received unless otherwise noted. PET, PEEK, and nylon 6/6 were obtained from Goodfellow, Inc. Acetonitrile was dried over $CaH_2$; and tetrahydrofuran (THF) was dried over KOH overnight. Both were distilled prior to use. Surface modified samples were analyzed using a Midac M25 10C interferometer equipped with a surface optics SOC4000 SH specular reflectance head attachment. Fluorimetry experiments utilized a Photon Technology International Fluorescence Spectrometer.

Polymer substrates (nylon 6/6, PET or PEEK) were placed in a deposition chamber equipped with two stopcocks for exposure either to vacuum or to the vapor of zirconium tetra(tert-butoxide). The chamber was evacuated at $10^{-3}$ torr for 1 hour and polymer slides were exposed to vapor of zirconium tetra(tert-butoxide) (with external evacuation) for 1 minute followed by 5 minutes exposure without external evacuation. This cycle was repeated twice, after which a heating tape was applied to the chamber, and the internal temperature of the chamber was raised to 60° C. and kept at that temperature for 5 minutes (without external evacuation). The chamber was then allowed to cool and was then evacuated at $10^{-3}$ torr for 1 hour to ensure removal of excess zirconium tetra(tert-butoxide) and to give surface activated polymers. AFM section analysis showed the zirconia film to be thin. IR analysis shows that some tert-butoxy groups remain in the deposited and pyrolyzed film.

Experiments with zirconium tetra(tert-butoxide) employing the following polymers and resins were performed with good results: polyimide Kapton®, polylactide-co-glycolate (PLGA), poly-3-hydroxybutyrate-co-valerate (PHBCV), Gore-Tex, and Aramide. It is to be expected that similar treatment of other polymers will yield similar results.

Activated polymers as prepared were treated with an aqueous solution of a copper salt, which was absorbed onto the zirconium oxide adhesion layer. Treatment with either sodium borohydride or an amine borane gave a copper-coated polymer. Electron dispersive X-ray based analysis showed the presence of both copper and zirconium.

Similarly, silver nitrate was used to deposit silver metal onto activated PET. It is to be expected that similar treatment of other polymers will yield similar results, as will the use of other metal salts using similar reducing agents.

Example 2. Electroless Plating of Copper

A sample of Kapton treated first with the zirconium-based adhesion layer, then copper sulfate, and then diethylamineborane as described in Example 1 was placed in a copper plating bath at 60° C. under nitrogen. The bath consisted of 0.1 M trisodium citrate dihydrate, 1.2 M ethylenediamine, 0.1 M copper sulfate hydrate, 0.03 M ferrous sulfate hydrate, $6.4 \times 10^{-4}$ M 2,2-dipyridine, 1.2 M NaCl, and sufficient sulfuric acid to give pH=6. A small amount of PEG 200 (2.5 mg) was added to a 50 ml bath.

Example 3. Polymer Metallization

The zirconium oxide/alkoxide adhesion layer nucleates the growth of copper metal on PET and Kapton® polyimide film surfaces; this approach provides a basis for patterned metallization of polymer-based device substrates.

The adhesion layer can serve as a matrix to enable polymer surface metallization. In a typical procedure Kapton® polyimide film was coated with a 5 nm thick layer of adhesion layer and was then soaked in a 200 mM aqueous solution of $CuSO_4$. Samples were rinsed in deionized water, and EDX analysis confirmed the presence of Cu and S. After subsequent (slow) reduction by dimethylamine borane (1M, aqueous, 6 hrs, 50° C.), metallic copper was formed. Metallization was also done using an adhesion layer patterned on Kapton® polyimide film. The metallized surface was subjected to sonication in water and physical rubbing with a Q-tip, which was followed by EDX. In this way it was shown that patterns of both Zr and Cu on the Kapton® polyimide film surface faithfully replicated the mask design.

A corresponding pattern was also observed by AFM. The thickness of the generated copper "seed" was measured via AFM to be ca. 20 times thicker than the starting film of adhesion layer, indicating the adhesion layer nucleates the growth of $CuSO_4$ at the polyimide surface. $CuSO_4$-treated Kapton® polyimide film was reduced rapidly using aqueous sodium borohydride, which also gave copper metal; here, AFM analysis showed the Cu pattern to be buried into the polymer surface in pits, the tops of which in many cases were about 500 nm below the polymer surface. It is believed that the relatively faster borohydride reduction is sufficiently exothermic so that the polymer melts in the vicinity of the reduction reaction.

Because the adhesion layer is thin (ca. 5 nm), it is resistant to cracking by physically flexing the polymer, therefore the adhesion layer is a suitable matrix for polymer metallization with copper. Copper "seed" layers can serve as nucleation sites for bulk copper growth by electroless deposition processes (Gu et al., Organic Solution Deposition of Copper Seed Layers onto Barrier Metals. Mat. Res. Soc. Symp. Proc. 2000, 612, D9.19.1-D9.19.6 (p. D9.19.2, lines 33-40; p. D9.19.5, lines 14-22)). In conjunction with photolithographic patterning, this further metallization of the polymer provides a means to prepare copper-based anti-infective compounds on a variety of flexible substrates under simple laboratory conditions.

Metallization of Kapton® polyimide film and PET. Patterned or un-patterned copper metallization of the polymer surfaces was achieved by soaking an activated polymer surface in a 200 mM aqueous solution of $CuSO_4$ overnight, followed by reduction in 1M aqueous dimethylamine borane or sodium borohydride for 6 hrs. Copper metallization was confirmed by Energy Dispersive X-ray Analysis, which was done using a FEI XL30 FEG-SEM equipped with a PGT-IMIX PTS EDX system.

Functionalized Organophosphorous Techniques

Substrates may be functionalized using functionalized organophosphorous techniques. See, U.S. Patent Application Publication 2004/0023048, incorporated herein by reference in its entirety. The organophosphonic acid-based segment may be derived from a functionalized organophosphonic acid such as an omega-functionalized organophosphonic acid containing a hydrocarbon ligand having from about 2 to about 40 carbon atoms, wherein the hydrocarbon ligand is a linear or branched, saturated or unsaturated, substituted or unsubstituted, aliphatic or aromatic alkylene moiety.

Substituents on the hydrocarbon portion of phosphonic acids useful in accordance with the present disclosure may be appended to any carbon atom of the hydrocarbon ligand. Useful substituents are, for example, reactive functional groups, for example, a hydroxyl group, carboxylic group, an amino group, a thiol group, a phosphonate group, and chemical derivatives thereof. It will be appreciated that any functional group which can participate in a further derivatization reaction can be employed. Additionally, an alkylene hydrocarbon ligand may contain within the structure or appended to the structure, reactive moieties, for example sites of unsaturation, which may be further reacted in a polymerization reaction with reactive substituents on the hydrocarbon ligands appended to other phosphonate sites bound to the surface of the native oxide during a phosphonate derivatizing reaction. In this manner, a phosphonate-organo-polymeric layer may be formed on the oxide surface. An example of such a polymerization reaction is the preparation of a surface coating of an acrylic derivative of a phosphonic acid. When acrylate and methacrylate substituents are employed, the polymerization proceeds spontaneously upon exposure to light or air. For less reactive coatings, the polymerization can be performed by exposing the coating to conventional polymerization reagents and conditions.

In some embodiments, coatings are formed from phosphonic acids having an organic ligand functionalized at a carbon of the ligand which is further reacted to form covalent bonds with anti-infective agents. For functionalized phosphonic acids, the application of the acid to oxide surface generally results in a self-assembled phosphonic acid film with a carbon directed away from the substrate surface and available for covalent bonding or further chemical modification. Preferred functional groups include hydroxyl, amino, carboxylate, thiol, and phosphonate groups.

It will also be appreciated that the reactive substituents pendent on the organic portion of a phosphonate bound to the oxide surface can be further reacted with reagents which are subject to hydrolysis reactions. Examples include metal alkoxides, examples of which are those having the structure $M(O-R)_n$, where M is a metal, R is a linear or branched, saturated or unsaturated, aliphatic or aromatic, substituted or unsubstituted hydrocarbon moiety, and "n" is equal to a stable valance state of the metal. Examples of metal alkoxide compounds are zirconium tetra(tert-butoxide), titanium tetra(tert-butoxide), and silicon tetra(tert-butoxide) where R is a t-butyl group, M is respectively Zr, Ti, and Si, and "n" is four. It will be appreciated that other hydrolytically reactive compounds which have two or more alkoxide ligands in addition to other ligands may also be utilized. For example, calcium alkoxides such as calcium bis(2-methoxy-ethoxide) may be employed. In general, alkoxide ligated metals in groups 2 through 14 will find utility in these secondary functionalization reactions with phosphonate coatings of the present development.

A process for forming a coated article by the foregoing technique may include (a) depositing a layer of a functionalized organophosphorous compound on an oxide substrate; (b) heating the substrate of step (a) to a temperature sufficient to bond the functionalized organophosphorous compound to the oxide substrate; (c) depositing a separate layer onto the layer produced by step (b); and (d) bonding the layers produced by steps (b) and (c) through the functional group.

Preferred functional groups are hydroxyl-, carboxylate-, amino-, thiol-, and phosphonato-functional groups, or these groups further derivatized by reaction with a metal or organo-metal reagent, for example an alkoxide. The groups participate in further bonding with moieties of the organic, inorganic or bioactive coating layer, either through strong chemical bonding, for example, covalent bonding, or through weaker bonding interactions, for example, hydrogen bonding.

Preferred metal reagents for derivatizing functional groups are metal alkoxides, for example zirconium tetra (tert-butoxide), silicon tetra(tert-butoxide), titanium tetra (tert-butoxide), and calcium bis(2-methoxy-ethoxide).

A preferred method of attaching an anti-infective agent to a native oxide surface comprises providing a phosphorous-based coating layer as described above wherein the functionalized organophosphonate moieties are hydroxyl, amine or thiolate that have been derivatized with a cross-coupling reagent such as (p-nitrophenyl) chloroformate, and further reacted with an amino or hydroxylated moiety, wherein the amino or hydroxylated moieties are a diamine or aminoalcohol bonded by a carbon-nitrogen bond or a carbon-oxygen bond, respectively, to a carbonyl group, the reaction providing a urethane, carbonate, urea, thiocarbonate, or thiourea bond to the derivatized functional group; the terminal amino group is then quaternized.

In accordance with another embodiment of the present invention there is provided a method of bonding a layer of a phosphorous-based acid moiety to a surface such as but not limited to an oxide surface (such as titanium, zirconium and tantalum oxide) comprising coating said oxide surface with a phosphorous-based acid moiety self-assembled layer and heating said coated oxide surface until the self-assembled layer is bonded thereto, the phosphorous-based acid moiety comprising the self-assembled layer being selected from the group consisting of phosphoric acid and organophosphonic acids.

Preferred coatings are those which have been formed from alkyl, alkylene- and arylene-organophosphonic acids, including substituted alkyl, alkylene and arylene-phosphonic acids. More preferred are substituted alkyl and alkylene phosphonic acids with a reactive substituent to the phosphonic acid functional group. Preferred oxide surfaces are the native oxide surfaces of titanium, zirconium and tantalum materials.

Functionalization of a Silicon Surface with a Self-Assembled Film of an Organophosphonic Acid Self-assembled films of an organophosphonic acid may be bonded to the native or synthesized oxide-coated silicon surface as a film of the corresponding phosphonate. Midwood et al., Easy and Efficient Bonding of Biomolecules to an Oxide Surface of Silicon. *Langmuir* 2004, 20, 5501-5505, incorporated herein by reference in its entirety. The phosphonate film is functionalized to enable covalent coupling of biological molecules that may be anti-infective; covalent coupling of anti-infective agents or moieties; and/or covalent coupling of anti-infective agents or moieties to a biological molecule. As with all functionalizing techniques disclosed herein, the functionalized surfaces and/or the anti-infective agents may be patterned on a substrate, depending on the particular application.

Functionalization of Titanium with Peptides.

Peptide-modified surface-bound phosphonate films may be easily prepared with high surface coverage. Gawalt et al., Bonding Organics to Ti Alloys: Facilitating Human Osteoblast Attachment and Spreading on Surgical Implant Materials" *Langmuir* 2003, 19, 200-204, incorporated herein by reference in its entirety. Anti-infective peptides may be bound to functionalized surfaces in accordance with the techniques described in Gawalt.

Organic anti-infective moieties that may be added to a functionalizing layer such as those described hereinabove include quaternary ammonium alkylamines, quaternary ammonium alkanols, usinic acid; cationic peptides such as cecropins neutrophil defensins, polyphemusin, gramicidins, thionins, histone-derived compounds, beta-hairpin, hemoglobin, lactoferrin; anionic peptides such as neuropeptide precursors, aromatic dipeptides, hemocyanin derivatives; other antimicrobial peptides such as bacteriacins, cathelicidin, thrombocidin, and histanins; antibodies, antibiotics, including tetracyclines, amphenicols, penicillins, cephalosporins, monobactams, carbapenems, sulfanomides, trimethoprim, macrolides, lincosamides, streptogramins, streptomycins, quinolones, glycopeptides, polymyxins, imidazole derivatives, nitrofuran derivatives; steroids; chlorhexidine; phenol compounds including triclosan; epoxides; polymers and/or polypeptides which have anti-infective properties.

Inorganic anti-infective coating layers that may be bonded include silver, copper, zinc oxides, titanium oxides, zeolites, silicates, calcium hydroxide, iodine, sodium hypochlorite, sulfites, and sulfates.

Preferred anti-infective moieties are quaternary ammonium compounds, such as benzethonium chloride, cetrimonium bromide, cetrimonium chloride, dimethyldioctadecylammonium chloride, tetramethylammonium hydroxide; quaternary ammonium alkyl dendrimers, silver, copper, cationic species such as benzalkonium chloride, Bronidox; and alkylated choline.

Compositions and devices in accordance with the present invention include but are not limited to any device(s) specific to an application by an orthopedic, cardiovascular, plastic, dermatologic, general, maxillofacial or neuro surgeon or physician including, but not limited to, cardiovascular or vascular implant device such as stents, replacement heart valves, replacement heart valve components, leaflets, sewing cuffs, orifices, annuloplasty rings, pacemakers, pacemaker polymer mesh bags, pacemaker leads, pacing wires, intracardiac patches/pledgets, vascular patches, vascular grafts, intravascular catheters, and defibrillators; tissue scaffolds; non-woven meshes, woven meshes, and foams; orthopedic implant devices including orthopedic trauma implants, joint implants, spinal implants, plates, screws, rods, plugs, cages, pins, nails, wires, cables, anchors, scaffolds, artificial joints selected from hand joints, wrist joints, elbow joints, shoulder joints, spine joints, hip joints, knee joints and ankle joints; bone replacement, bone fixation cerclage and dental and maxillofacial implants; spine implant devices including intervertebral cages, pedicle screws, rods, connectors, cross-links, cables, spacers, facet replacement devices, facet augmentation devices, interspinous process decompression devices, interspinous spacers, vertebral augmentation devices, wires, plates, spine arthroplasty devices, facet fixation devices, bone anchors, soft tissue anchors, hooks, spacing cages, and cement restricting cages; diagnostic implants, biosensors, glucose monitoring devices, external fixation devices, external fixation implants, dental implants, maxillofacial implants, external facial fracture fixation devices and implants, contact lenses, intraocular implants, keratoprostheses; neurosurgical devices and implants selected from shunts and coils; general surgical devices and implants selected from drainage catheters, shunts, tapes, meshes, ropes, cables, wires, sutures, skin and tissue staples, bone anchors, soft tissue anchors, burn sheets, and vascular patches; and temporary/non-permanent implants. Specifically, such devices include an anti-infective agent to counter infective agents.

EXAMPLES

Derivatization of Adhesion Layer Via Organophosphorous Interfaces

A zirconium oxide/alkoxide adhesion layer was deposited onto Nylon 6/6 and then reacted with a solution of 11-hydroxyundecylphosphonic acid to form an organophosphonate monolayer. See, Dennes, T. J. et al., High-Yield Activation of Scaffold Polymer Surfaces to Attach Cell Adhesion Molecules. *J. Am. Chem. Soc.* 2007, 129, 93-97, incorporated herein by reference in its entirety. Experimental details appear at page 95, col. 1-page 97, col. 1; see also discussion at pages 94-96 and accompanying figures.

The substrate was first immersed in a solution of 3-(maleimido)propanoic acid N-hydroxysuccinimide ester and then in an aqueous solution of RGDC to derivatize the phosphonate monolayer with an active peptide. In a prophetic example, an anti-infective peptide may be bound to the phosphonate monolayer in place of RGD.

Antibody Coupling Using Functionalized Organophosphonates

11-Hydroxyundecylphosphonic acid was reacted with the surface of cleaned and prepared silicon wafers, forming a self-organized 11-hydroxyundecylphosphonate monolayer on $SiO_2$. This was confirmed by QCM and AFM. The omega-functional groups were derivatized using disuccinimidyl glutarate (DSG) in dry acetonitrile. Rabbit antimouse IgG (Pierce) was then coupled to the derivatized monolayer by incubating for 30 min at a concentration of 100 ig/mL in PBS. Antibody coupling was accomplished by incubation with 10 ig/mL anti-R4 integrin antibody P1H4 (Chemicon) or anti-R5 integrin antibody SAM-1 (Cymbus Technology Ltd.) for 2 h. Antibody activity was confirmed by incubation of CHOα4 or CHOα5 cells; selective cell growth indicated appropriate activity.

In a prophetic example, a self-assembled monolayer of 11-hydroxyphosphonate is bonded to the native oxide surface of titanium and is then treated first with (p-nitrophenyl) chloroformate and then a solution of 1,12-diaminododecane (Aldrich) to give an aminododecyl urethane bonded to the titanium through the phosphonate interface. The distal amino group is then quaternized using octyl iodide (Aldrich) to give the quaternary alkylammonium moiety covalently bonded to the substrate through the phosphonate interface.

Similarly, in a prophetic example, a quaternary alkylammonium moiety may be bonded to a polymer such as PEEK by first preparing an adhesion layer of zirconium oxide on the PEEK surface followed by treatment with the 11-hydroxyphosphonic acid to give the 11-hydroxyphosphonate monolayer bonded to the PEEK. The 11-hydroxyphosphonate monolayer is derivatized by reaction, sequentially, with (p-nitrophenyl) chloroformate, 1,12-diaminododecane, and octyl iodide.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

All references cited herein are incorporated fully by reference.

The invention claimed is:

1. A method of preparing a medical device having an anti-infective surface, the method comprising
    covalently bonding a functionalized organophosphonate to a native oxide surface of a metal,
    derivatizing the functionalized organophosponate, and
    covalently bonding a quaternary ammonium anti-infective agent to the organophosphonate,
    wherein the functionalized organophosphonate is an hydroxy, amino or thiol omega-functionalized organophosphonate where the organo group is a linear or branched, saturated or unsaturated, substituted or unsubstituted, aliphatic or aromatic alkylene hydrocarbon of from 2 to 40 carbon atoms, and
    comprising derivatizing the hydroxy, amino or thiol with a cross-coupling reagent;
    reacting the derivatized hydroxy, amino or thiol with a diamine or aminoalcohol to bond the organo group of the organophosphonate via a urethane, carbonate, urea, thiocarbonate or thiourea bond and provide a distal amino group; and
    quaternizing the distal amino.

2. The method according to claim 1 comprising covalently bonding the functionalized organophosphonate directly to the native oxide surface.

3. The method according to claim 1 comprising contacting a metal alkoxide with the native oxide surface, subjecting the metal alkoxide to conditions adequate to form a metal oxide adhesion layer, the conditions selected from the group consisting of pyrolysis, microwaving, complete or partial hydrolysis, and covalently bonding a functionalized organophosphonate to the metal oxide adhesion layer.

4. The method of claim 3 comprising contacting a zirconium alkoxide with the native oxide surface.

5. The method of claim 3 comprising contacting a zirconium alkoxide with a native oxide surface of titanium.

6. The method of claim 1 wherein the organophosphonate is 11-hydroxyundecylphosphonate.

7. The method of claim 1 wherein the the anti-infective agent is a quaternary alkylammonium moiety.

8. The method of claim 1 wherein the metal is selected from the group consisting of titanium, stainless steel, cobalt chrome, nickel, molybdenum, tantalum, zirconium, magnesium, manganese, niobium, and alloys thereof.

9. The method of claim 1 wherein the metal is titanium.

* * * * *

UNITED STATES PATENT AND TRADEMARK OFFICE
CERTIFICATE OF CORRECTION

PATENT NO. : 10,596,304 B2
APPLICATION NO. : 15/497909
DATED : March 24, 2020
INVENTOR(S) : Randell Clevenger et al.

Page 1 of 1

It is certified that error appears in the above-identified patent and that said Letters Patent is hereby corrected as shown below:

In the Specification

Column 1, Line 11 Add the following Statement Regarding Federally Sponsored Research:
"This invention was made with government support under Grant No. CHE-0612572 awarded by the National Science Foundation. The government has certain rights in the invention."

Signed and Sealed this
Fourteenth Day of July, 2020

Andrei Iancu
*Director of the United States Patent and Trademark Office*